United States Patent [19]

Bous

[11] Patent Number: 5,489,396
[45] Date of Patent: Feb. 6, 1996

[54] CLEANING/DECONTAMINATING LIQUID COMPOSITIONS BASED ON ALKOXYLATED SURFACTANT MIXTURES, PARTICULARLY FOR EMERGENCY SETS, AND THEIR USE

[76] Inventor: Klaus Bous, P.O. Box 3039, Sherwood Park, Alberta, Canada, T8A 2A6

[21] Appl. No.: 211,419

[22] PCT Filed: Sep. 25, 1992

[86] PCT No.: PCT/EP92/02223

§ 371 Date: May 20, 1994

§ 102(e) Date: May 20, 1994

[87] PCT Pub. No.: WO93/05764

PCT Pub. Date: Apr. 1, 1993

[30] Foreign Application Priority Data

Sep. 26, 1991 [DE] Germany ............... 41 32 129.4
Oct. 2, 1991 [DE] Germany ............... 41 32 886.8

[51] Int. Cl.⁶ ............... C11D 1/825; C11D 3/48; A61K 7/50
[52] U.S. Cl. ............... 252/174.22; 252/106; 252/174.17; 252/DIG. 5; 252/DIG. 14
[58] Field of Search ............... 252/174.22, 174.21, 252/DIG. 1, 106, 107, 108, 174.17, 174.18, DIG. 5, DIG. 14

[56] References Cited

U.S. PATENT DOCUMENTS

| | | | |
|---|---|---|---|
| 2,617,754 | 11/1952 | Neely | 424/63 |
| 3,934,003 | 1/1976 | Tuma et al. | 424/59 |
| 4,154,706 | 5/1979 | Kenkare | 252/547 |
| 4,247,425 | 1/1981 | Egan et al. | 252/548 |
| 4,256,611 | 3/1981 | Egan et al. | 252/548 |
| 4,261,851 | 4/1981 | Duke | 252/174.21 |
| 4,426,310 | 1/1984 | Verunica | 252/106 |
| 4,450,091 | 5/1984 | Schmolka | 252/174.21 |
| 4,456,543 | 6/1984 | Owens | 252/106 |
| 4,544,495 | 10/1985 | Schmolka | 252/174.21 |
| 4,774,016 | 9/1988 | Gazzani | 252/170 |
| 4,818,440 | 4/1989 | Schäfer et al. | 252/546 |
| 4,897,214 | 1/1990 | Gazzani | 252/170 |
| 4,898,690 | 2/1990 | Bitter et al. | 252/554 |
| 5,021,185 | 6/1991 | Mustakallio | 252/142 |
| 5,025,069 | 6/1991 | Deguchi et al. | 252/174.17 |
| 5,154,850 | 10/1992 | Deguchi et al. | 252/174.17 |
| 5,173,216 | 12/1992 | Uhlig | 252/547 |
| 5,290,479 | 3/1994 | Clark | 252/351 |

FOREIGN PATENT DOCUMENTS

| | | |
|---|---|---|
| 0115888 | 8/1984 | European Pat. Off. . |
| 0408965 | 1/1991 | European Pat. Off. . |
| 0471606 | 2/1992 | European Pat. Off. . |
| 59-174800 | 10/1984 | Japan . |
| 2242686 | 10/1991 | United Kingdom . |
| 9109925 | 7/1991 | WIPO . |

*Primary Examiner*—Paul Lieberman
*Assistant Examiner*—A. E. Hertzog
*Attorney, Agent, or Firm*—Lowe, Price, LeBlanc & Becker

[57] ABSTRACT

A cleaning liquid contains as component (A) a polyalkyleneglycol monoalkylether and as component (B) a polyalkyleneglycol fatty acid partial glyceride, and optionally at least a non-ionogenic, surface-active liquid agent. This cleaning liquid is particularly useful for first aid sets and can be used for cleaning and/or decontaminating wounded and/or contaminated skin of human beings and animals, and for medical skin care and hygiene.

18 Claims, No Drawings

CLEANING/DECONTAMINATING LIQUID COMPOSITIONS BASED ON ALKOXYLATED SURFACTANT MIXTURES, PARTICULARLY FOR EMERGENCY SETS, AND THEIR USE

DESCRIPTION

This invention relates to a cleaning liquid, which is particularly intended for use in emergency sets, and its use as a general cleaning agent, as an agent for cleaning and/or decontaminating skin in the case of injuries and/or contaminations of human beings and animals and for a medical treatment of and for cleaning skin.

A large number of cleaning liquids are known, also for medical purposes. When they are used in the household or for medical purposes, they contain water as a main constituent, as a rule, to which various detergents have been added. For technical purposes, aqueous solvents are not yet regularly used as cleaning liquids although aqueous cleaning liquids are increasingly employed for ecological reasons.

As a rule, all said cleaning liquids have a defined composition, which render them particularly suitable for certain purposes. The composition also determines the limits of the application. For instance, aqueous cleaning liquids cannot be used, as a rule, at temperatures which are distinctly below the freezing point. On the other hand, it is not permissible to use highly volatile solvents in tropical regions. Owing to said restrictions a suitable cleaning agent is often not available in an emergency, e.g., in case of an accident or when an important part of a plant has been soiled or contamination with malodorous, soiling, toxic or etching substances has been effected. In such cases there is a demand for a cleaning agent which is of universal utility and is always ready at hand in a set or in a tear strip package. Such a cleaning agent should be usable in combination with and without water and after use should be suitable for being readily disposed of with the waste water or domestic refuse.

That object is accomplished in accordance with the invention by the provision of a cleaning liquid which contains as components (A) a polyalkyleneglycol monoalkyl ether and (B) a polyalkyleneglycol fatty acid partial glyceride and optionally at least one non-ionogenic liquid surface-active agent.

The cleaning liquid according to the invention is particularly suitable for use in emergencies. It may be used, e.g., as an agent for cleaning and/or decontaminating skin in the case of injuries and/or contaminations of human beings and animals. But it may also be used to clean and/or decontaminate surfaces, e.g., of machines, glass panes, furniture, plants, etc, and there are no special restrictions.

Whereas the cleaning liquid in accordance with the invention may be used or mixed with water it can preferably be applied without water or independently of water and in that case will have a quite comparable soil-removing cleaning or cleaning activity. It may be used to remove contaminating chemicals and will have also a certain detoxicating activity. It is substantially non-toxic and non-flammable and has a low volatility and will preserve its full utility at low temperatures far below the freezing point as well as at tropical temperatures. As a surface-cleaning agent it may replace conventional cleaners, such as gasoline, aromatic compounds, turpentine, alcohol, chlorinated hydrocarbons or ethers and esters.

The components A to D which are employed are commercially available substances, which are offered in the market for various purposes. Components C and D may be described as surface-active agents or surfactants, which have lipophilic and hydrophilic properties and are soluble in or compatible with water. But the components C and D may be replaced by conventional non-ionogenic surface-active agents, which individually or in combination have lipophilic and hydrophilic properties. It will be understood that components C and D may also be used in combination with further non-ionogenic surface-active agents. The non-ionogenic surface-active agents which have a conventional structure and those which have the structural formulas C and D may be soluble or insoluble in water. But it is important that the lipophilic and hydrophilic properties are balanced so that the cleaning liquid in accordance with the invention has the required application spectra.

The polyoxyalkyleneglycol monoalkyl ether used as components A is preferably a block cooligomer or block copolymer of propylene oxide and ethylene oxide having preferably up to 80 oxyalkylene units and up to 6 carbon atoms in the ether unit. A particularly preferred poloyoxyethylene-polyoxypropylene monoalkyl ether has either of the following formulas A

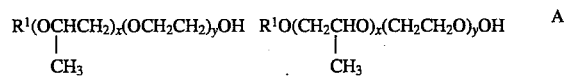

wherein $R^1$ is an alkyl residue having 1 to 5 carbon atoms, x equals 2 to 33, and y equals 3 to 45. The alkyl residue may particularly consist of the butyl residue although other straight-chain or branched alkyl residues having up to 6 carbon atoms may also be used. x has particularly a value of 9 to 20 and y a value from 10 to 30.

Component B may particularly consist of a polyalkyleneglycol monofatty acid glyceride of a fatty acid having 6 to 18 carbon atoms, particularly one having the following formula B:

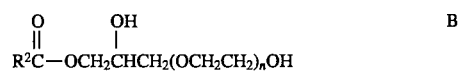

wherein $R^2$ is an alkyl or alkenyl having 5 to 17 carbon atoms and n equals 2 to 10. The glyceride preferably contains on an average six ethylene oxide units and $R^2$ is preferably an alkyl residue having 7 or 9 carbon atoms. Component B may alternatively consist of a polyoxyethylated fatty acid partial glyceride of a fatty acid having 5 to 18 carbon atoms.

The polyalkyleneglycol fatty acid partial glyceride of component B can in itself be regarded as a non-ionogenic surfactant or surface-active agent but must mainly be regarded as a cleaning and/or dissolving component.

In addition to components A and B the cleaning liquid in accordance with the invention selectively contains a non-ionogenic liquid surface-active agent, which is both lipophilic and hydrophilic. It is essential that said properties balance each other; this can be achieved with a surfactant which has been prepared to be lipophilic as well as hydrophilic, and with a combination of a lipophilic surfactant and a hydrophilic surfactant.

The non-ionogenic liquid surface-active agent may consist of a polyoxyalkylenesorbitol monofatty acid ester and/or a polyoxyalkylenesorbitan monofatty acid ester. The latter has particularly the following structure C

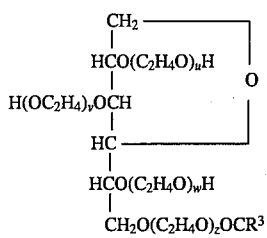

wherein $R^3$ is an alkyl residue or alkenyl residue having 7 to 21 carbon atoms and the sum u+v+w+z has an average value of 10 to 30. Particularly preferred are oleates in which the sum of u+v+w+z has an average of about 20. The sorbitan ester C may be present in a mixture with the corresponding sorbitol ester, in which the further hydroxyl functionalities may also be oxyalkylated.

The cleaning liquid may alternatively or additionally contain as a non-ionogenic liquid surface-active agent a polyoxyalkylene fatty alcohol ether, particularly one having the following formula D

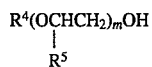

wherein $R^4$ is an alkyl residue having 6 to 20 carbon atoms, $R^5$ is H and/or $CH_3$, and m has an average value of 4 to 50. It is particularly preferred to use stearyl as $R^4$, to select an average value of about 15 for m, and to use $CH_3$ as $R^5$. But component D may also consist of a mixture of the polyoxyethylene and polyoxypropylene compounds or of a cooligomer or copolymer.

If components A and B are used in combination they will preferably be present in the cleaning liquid in accordance with the invention in a volume ratio of 1:1 to 4:1, particularly of about 2:1. Component C may be present in an amount of up to 40% by volume, preferably of about 20% by volume. Component D is suitably present in an amount of up to 20% by volume, preferably of about 6% by volume. The volume ratio A/B may also be 1:1 to 1:4.

Preferred compositions of the cleaning liquid in accordance with the invention contain the components A to D in the following proportions by volume: A 40 to 60%, B 20 to 30%, C 15 to 25%, and D 2 to 10%. The following composition has been found to be particularly suitable:

| | |
|---|---|
| A polyoxyethylene-polyoxypropylene monobutyl ether | 50% |
| B polyoxyethylene-octanoic/decanoic acid glycerides | 24% |
| C polyoxyethylenesorbitan monooleate | 20% |
| D polyoxypropylene stearyl ether | 6% |

The cleaning liquid according to the invention may contain, if required, conventional additives, such as stabilizers, dyestuffs, preservatives, disinfectants, odorous substances, etc. In some cases it may be proper, to prepare it as a cleaning gel, in which case it contains conventional thickening substances, if the natural viscosity is still not sufficient. Due to the fact that the cleaning liquid according to the invention may e.g. be present also as a gel, it is preferably characterized in as cleaning composition. The cleaning composition in accordance with the invention may also have a disinfecting activity per se, without further additives; for this reason it may be used as a disinfectant for human beings and animals and for objects. Whereas it is not necessary to use further additives, it is possible to admix additives which are known to those skilled in the art, such as other disinfectants. The cleaning composition in accordance with the invention may also be used as a basis of disinfectants (as a vehicle and adjuvant).

The cleaning composition in accordance with the invention may be used to decontaminate human beings and animals as well as objects, e.g., to remove toxins.

The cleaning composition in accordance with the invention may also be used as an agent for controlling skin diseases, such as parakeratoses, hyperkeratoses, seborrhoea, ichthyosis, acne, excema and other skin diseases, i.e., in general for the medical treatment and for the cleaning of the skin of human beings and animals.

What is claimed is:

1. A cleaning liquid, comprising
   (A) 40–60 volume % of a polyoxyethylene-polyoxypropylene monoalkyl ether compound selected from one of the following formulas A1 and A2

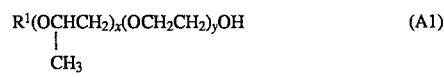

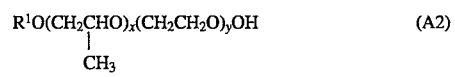

wherein $R^1$ is a $C_1$–$C_6$ alkyl group, x=2 to 33, and y=3 to 45;
   (B) 20–30 volume % of a polyalkyleneglycol monofatty acid glyceride of the formula B

wherein $R^2$ is an alkyl or alkenyl group having 5 to 17 carbon atoms, and n equals 2 to 10;
   (C) 15–25 volume % of a non-ionogenic liquid surface-active agent selected from the group consisting of a polyoxyalkylenesorbitol monofatty acid ester, a polyoxyalkylenesorbitan monofatty acid ester and a mixture thereof; and
   (D) 2–10 volume % of a polyoxyalkylene fatty alcohol ether of the formula D

wherein $R^4$ is stearyl, each $R^5$ is independently selected from H and $CH_3$, and m has an average value of 4 to 50.

2. A cleaning liquid according to claim 1, wherein $R^1$ is a butyl residue, x equals 9 to 20, and y equals 10 to 30.

3. A cleaning liquid according to claim 1, wherein $R^2$ is an alkyl residue having 7 or 9 carbon atoms and n has an average value of 6.

4. A cleaning liquid according to claim 1, wherein the polyoxyalkylenesorbitan monofatty acid ester has the formula C

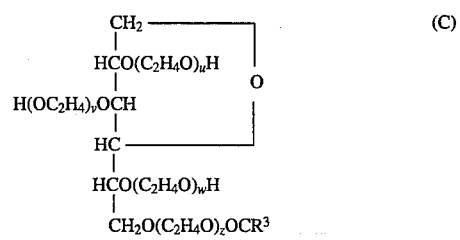

wherein $R^3$ is an alkyl residue or alkenyl residue having 7 to 21 carbon atoms and the sum of u+v+w+z has an average value of 10 to 30.

5. A cleaning liquid according to claim 4, wherein the ester of formula (C) is an oleate in which the sum of u+v+w+z has an average value of 20.

6. A cleaning liquid according to claim 1, wherein the volume ratio A:B is 4:1 to 1:4.

7. A cleaning liquid according to claim 6, wherein the volume ratio A:B is about 2:1.

8. A cleaning liquid according to claim 1, wherein component C is present in an amount of up to about 20% by volume.

9. A cleaning liquid according to claim 1, wherein component D is present in an amount of up to about 6% by volume.

10. A cleaning liquid according to claim 1, consisting essentially of 50% by volume component (A), 24% by volume component (B), 20% by volume component (C), and 6% by volume component (D).

11. A cleaning liquid according to claim 1, further comprising at least one additive selected from the group consisting of stabilizers, dyestuffs, preservatives, disinfectants and odorous substances.

12. A cleaning liquid according to claim 1, in the form of a viscous gel.

13. A method of cleaning skin, comprising applying to skin a cleaning liquid according to claim 1.

14. A method of medically treating skin, comprising applying to skin a cleaning liquid according to claim 1.

15. A method of decontaminating skin, comprising applying to skin a cleaning liquid according to claim 1.

16. A method of cleaning or decontaminating soiled surfaces, comprising applying to soiled surfaces a cleaning liquid according to claim 1.

17. A method of disinfecting a surface comprising applying to a surface a cleaning liquid according to claim 1.

18. A cleaning liquid according to claim 1, consisting essentially of components (A)–(D).

* * * * *